United States Patent [19]

Suzuki

[11] Patent Number: 5,719,659
[45] Date of Patent: Feb. 17, 1998

[54] OPHTHALMIC APPARATUS HAVING LIGHT POLARIZING MEANS

[75] Inventor: Takayoshi Suzuki, Hamamatsu, Japan

[73] Assignee: Kowa Company Ltd., Japan

[21] Appl. No.: 760,827

[22] Filed: Dec. 5, 1996

[30] Foreign Application Priority Data

Jul. 30, 1996 [JP] Japan ................................. 8-199886

[51] Int. Cl.⁶ ..................................................... A61B 3/10
[52] U.S. Cl. ........................................... 351/215; 351/205
[58] Field of Search ..................................... 351/215, 205, 351/206, 211, 221, 246, 200; 354/62

[56] References Cited

U.S. PATENT DOCUMENTS 5,537,162   7/1996   Hellmuth et al. ..................... 351/206

*Primary Examiner*—Hung X. Dang
*Attorney, Agent, or Firm*—Adams & Wilks

[57] ABSTRACT

An ophthalmic apparatus for diagnosing the condition of an eye based on an examination of images of interference fringes formed by a lacrimal layer on the anterior portion of the eye. The apparatus has an illumination system that projects a beam of light from a light source onto the anterior portion of the eye, and an imaging system, such as a CCD camera, that produces images of interference fringes formed by a lacrimal layer on the anterior portion of the eye. The illumination and imaging systems each have linear polarizers having mutually parallel linear polarization axes.

4 Claims, 2 Drawing Sheets

OPHTHALMIC APPARATUS HAVING LIGHT POLARIZING MEANS

BACKGROUND OF THE INVENTION

1. Field of the Invention

The present invention relates to an ophthalmic apparatus, and more particularly to an ophthalmic examination apparatus for diagnosing dry eye conditions by observation of a lacrimal layer formed on the anterior portion of an eye under examination.

2. Description of the Prior Art

Recent years have seen an increase in the numbers of people suffering from dry eyes caused by reduced lacrimation brought on by working with VDTs (visual display terminals) or working in rooms in which the air is dried out by air conditioning systems. Dry eyes can lead to a number of eye ailments including damage to the corneal epithelium and conjunctiva. For this reason, the diagnosis of dry eye syndrome is becoming an important part of ophthalmic diagnostic procedure.

Conventional methods of diagnosing dry eye include examining vital stains and quantity of lacrimal fluid. However, such methods involve discomfort to the patient caused by the application of a solution or contacting the eye with an instrument. Methods were then proposed involving projecting a beam of coherent light onto the eye and examining interference fringes formed by the lacrimal layer. The disclosures of JP-B-62-222143, JP-B-7-136120 and JP-A-6-189743 are examples of such methods. In the apparatus of such systems, color images of interference fringes (interference patterns of color changes in the iris) formed by the oily film on the lacrimal layer are converted by a photoelectric element in a light-receiving system and shown on a display means. The presence of dry eye can then be readily diagnosed by examining the interference pattern indicating the condition of the lacrimal layer.

However, a problem with the interference fringes produced with the conventional systems is the low contrast of the fringes. The reason for this is that in the conventional apparatuses, the eye is illuminated using a natural light source (randomly polarized light). Interference fringes are produced by components of light having the same linear polarization. If illumination is by randomly polarized light, the presence of so many unlike components means that a large proportion of the light components do not contribute to the interference, and these non-contributing components form a large background (DC) component that lowers the contrast of the interference pattern. The low contrast makes it difficult to make a good diagnosis based on the interference fringes.

The object of the present invention is to provide an ophthalmic apparatus that enables interference fringes formed by a lacrimal layer on a target eye to be observed with good clarity by increasing the contrast of the interference fringes.

SUMMARY OF THE INVENTION

In accordance with the present invention, this object is attained by an ophthalmic apparatus in which interference fringes formed by a lacrimal layer on an anterior portion of a target eye are imaged and the target eye is diagnosed based on the imagedinterference fringes, said apparatus comprising an illumination optical system that illuminates an anterior portion of an eye, an imaging optical system that images interference fringes formed by a lacrimal layer on the anterior portion of the eye illuminated by the illumination system, and a linear polarizer disposed in the illumination system and a linear polarizer disposed in the imaging system having mutually parallel linear polarization axes.

The object is also attained by an ophthalmic apparatus in which interference fringes formed by a lacrimal layer on an anterior portion of a target eye are imaged and the target eye is diagnosed based on the imaged interference fringes, said apparatus comprising a light source that produces light linearly polarized in a prescribed direction, an illumination optical system that illuminates an anterior portion of an eye with light from the light source, an imaging optical system for imaging interference fringes formed by a lacrimal layer on the anterior portion of the eye illuminated by the illumination system, and a linear polarizer disposed in the imaging system having a linear polarization axis that is parallel to the linearly polarized light from the light source.

The light beam projected onto the lacrimal layer is transformed by the linear polarizer into light having the same linear polarization components (or such light is produced by the light source). Therefore, reflected light from the front and rear surfaces of the lacrimal layer has high coherence, forming interference fringes exhibiting high contrast. These interference fringes are acquired by a CCD camera, after passing through a linear polarizer having the same polarization axis as the illumination system polarizer. The interference fringes imaged by the CCD camera have a large AC component, while the DC component, which does not contribute to the interference, is small, so the contrast of the interference fringes is enhanced.

In a preferred embodiment, the direction of polarization by a polarizer can be varied to maximize the intensity, and hence the contrast, of the interference fringes being observed and imaged.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENT

An embodiment of the invention will now be described in detail with reference to the drawings.

Figure 1:
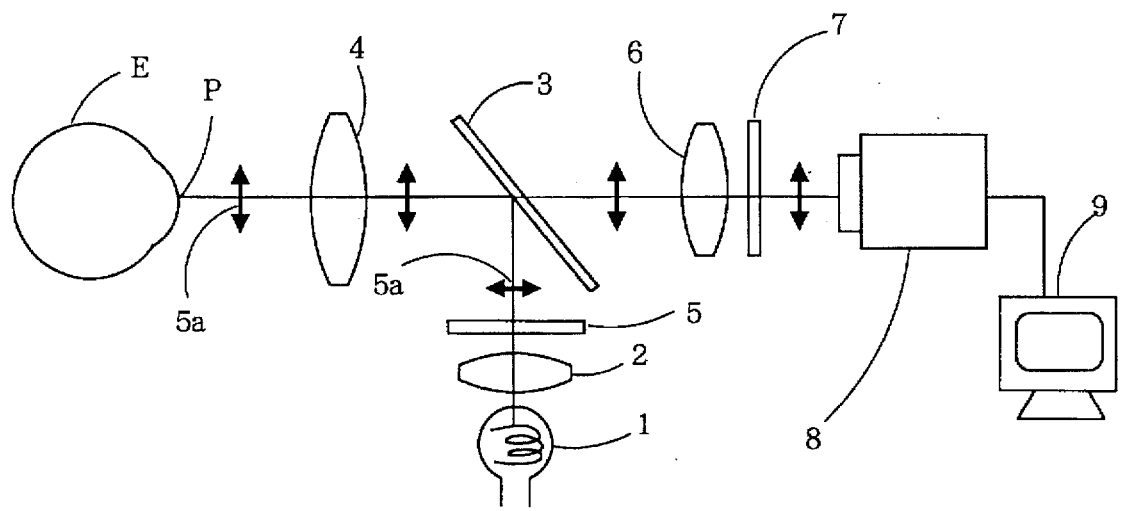
FIG. 1 is a diagram of the optical system in the ophthalmic apparatus according to the present invention.

FIG. 1 shows the general configuration of the ophthalmic apparatus of the invention, in which the reference numeral 1 denotes a halogen lamp or other such white light source for illuminating a target eye E. A beam of light from the light source 1 goes via a lens 2 and a half-mirror 3 to illuminate a prescribed point P on the eye E. A point P location is selected that is on the outermost fatty layer of the lacrimal layer on the cornea of the eye E. A linear polarizer 5 is disposed on the light path between the lens 2 and the half-mirror 3. This polarizer 5 linearly polarizes light in a prescribed direction (that, with reference to the drawing, is parallel to the surface of the drawing sheet). The amount of light emitted by the light source 1 can be regulated by a light adjustment circuit (not shown).

Reflected light from point P (reflected light from the front and back surfaces of the fatty layer on the outermost part of the lacrimal layer) forms various interference fringes, the fringes actually formed depending on the thickness of the fatty layer and other conditions. The reflected light forming the interference fringes is received by a color CCD camera 8, to which the reflected light is guided by the lens 4, the half-mirror 3 and a lens 6. A linear polarizer 7 having a prescribed linear polarization axis is located on the light path between the lens 6 and the camera 8. The polarizer 7 polarizes light in the same direction as the linear polarizer 5, which is to say, parallel to the sheet surface in the case of FIG. 1.

Color images of the interference fringes are converted to RGB video signals by the camera 8, stored in a video storage apparatus (not shown) and/or displayed on a monitor 9. The video information thus stored or displayed is used to diagnose dry eye.

In this arrangement, the white light source 1 is turned on to emit a beam of light that is projected onto the lacrimal fatty layer on the cornea, via lens 2, linear polarizer 5, half-mirror 3 and lens 4. The light from the light source 1 is linearly polarized by the polarizer 5, forming a polarized light component that, as indicated by 5a, is parallel to the drawing sheet. Reflected light from the front and back surfaces of the lacrimal layer passes via the lens 4, half-mirror 3, lens 6 and polarizer 7 and is received on the CCD light-receiving face of the camera 8, via which color images of the interference fringes are displayed on the monitor 9.

Figure 3:
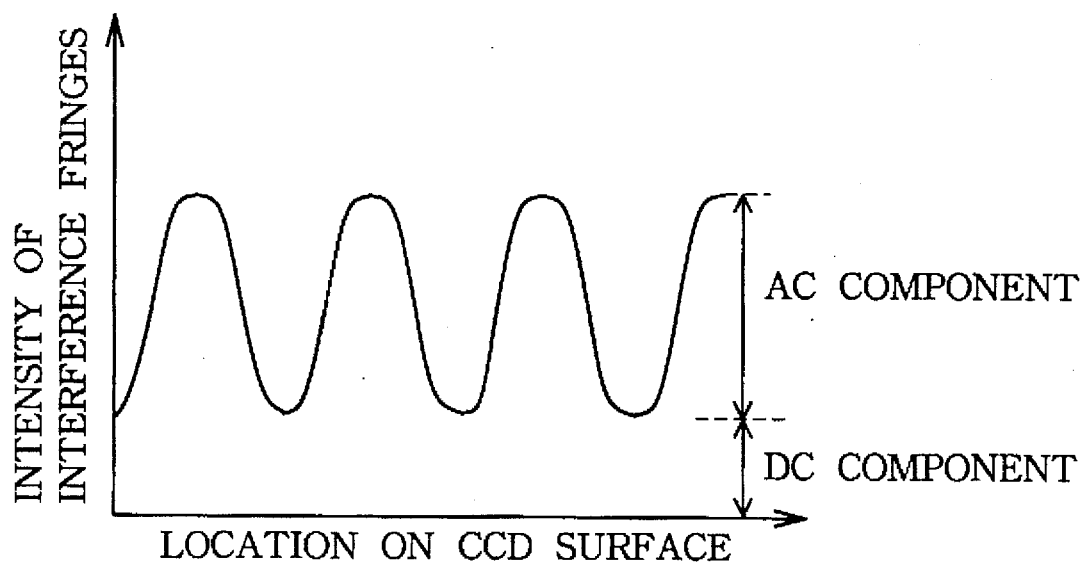
FIG. 3 is a diagram showing the intensity of interference fringes formed on the anterior portion of an eye.

Thus, in the arrangement shown in FIG. 1 the illumination system (parts 1, 5, 3 and 4) has its linear polarizer 5 and the image acquisition system (parts 4, 3, 6 and 8) has its linear polarizer 7. Since the light beam projected onto the lacrimal layer of the cornea is polarized to form a linear polarized light component 5a that is substantially parallel to the drawing sheet, the coherency of the reflected light from the front and back surfaces of the lacrimal layer is increased, resulting in high-contrast interference fringes with a large AC component. Since the interference fringes thus formed are received by the camera 8 after passing through polarizer 7, which has the same polarization axis as polarizer 5, the intensity of the interference fringes is not attenuated. The result is that, as shown in FIG. 3, the interference fringes imaged by the camera 8 have a large AC component, while the DC component, which does not contribute the interference, is small, producing high-intensity, high-contrast fringes.

Figure 2:
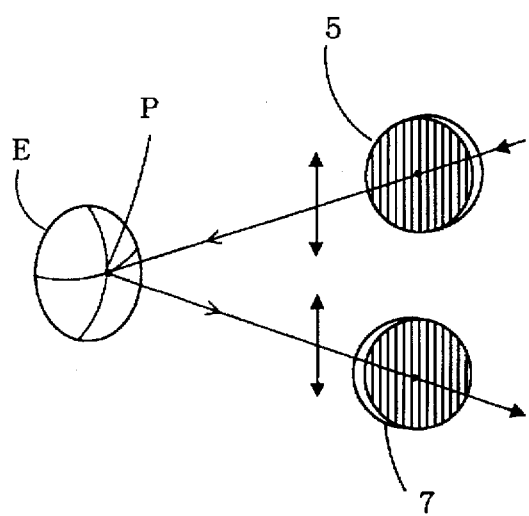
FIG. 2 is a diagram illustrating light polarized by a linear polarizer.

FIG. 2 shows how the light beam formed into the prescribed linearly polarized component by the polarizer 5 is projected onto the cornea P, and reflected light from the cornea passes through the polarizer 7 having the same polarization axis as the polarized light reflected by the lacrimal layer. FIG. 2 is drawn to illustrate the polarization of the light by the polarizers in a way that is easy to comprehend, and as such, it should be understood that it may not necessarily be fully consistent with the polarization arrangement shown in FIG. 1.

Moreover, in the above-described example both polarizers have a fixed polarization axis. However, the invention is not limited thereto. Instead, an arrangement may be used in which the polarizer 7 can be rotated about the optical axis, to allow it to be adjusted until the fringes being observed are at maximum intensity. Similarly, in cases where the contrast or intensity of fringes is also related to the polarization axis of the polarizer 5, an arrangement may be used that allows the axis to be adjusted, such as by rotating the polarizer 5 about the optical axis. Moreover, instead of the randomly polarized white light source used in the arrangement of FIG. 1, a light source may be used that produces light linearly polarized in a prescribed direction.

As described in the foregoing, in accordance with the present invention, the lacrimal layer is illuminated by means of an illuminating system with light polarized in a prescribed direction, so reflected light from the front and rear surfaces of the lacrimal layer has high coherency, resulting in the formation of high-contrast interference fringes. Images of these interference fringes are obtained via a polarizer having the same polarization axis as the linear polarized light of the illumination system, producing high-intensity, high-contrast fringe images. As a result, the high-sensitivity detection of lacrimal abnormalities is facilitated.

What is claimed is:

1. An ophthalmic apparatus in which interference fringes formed by a lacrimal layer on an anterior portion of a target eye are imaged and the target eye is diagnosed based on the imagedinterference fringes, said apparatus comprising:

an illumination optical system that illuminates an anterior portion of an eye;

an imaging optical system that images interference fringes formed by a lacrimal layer on the anterior portion of the eye illuminated by the illumination system; and a linear polarizer disposed in the illumination system and a linear polarizer disposed in the imaging system having mutually parallel linear polarization axes.

2. The apparatus according to claim 1, in which the direction of linear polarization by one or both linear polarizers is variable.

3. An ophthalmic apparatus in which interference fringes formed by a lacrimal layer on an anterior portion of a target eye are imaged and the target eye is diagnosed based on the imagedinterference fringes, said apparatus comprising:

a light source that produces light linearly polarized in a prescribed direction;

an illumination optical system that illuminates an anterior portion of an eye with light from the light source;

an imaging optical system for imaging interference fringes formed by a lacrimal layer on the anterior portion of the eye illuminated by the illumination system; and a linear polarizer disposed in the imaging system having a linear polarization axis that is parallel to the linearly polarized light from the light source.

4. The apparatus according to claim 3, in which the direction of linear polarization by the linear polarizer is variable.

* * * * *